United States Patent [19]

Lee et al.

[11] Patent Number: 5,080,657

[45] Date of Patent: Jan. 14, 1992

[54] ALGINIC

[75] Inventors: Hae B. Lee; Byung C. Shin, both of Daejun, Rep. of Korea

[73] Assignee: Korea Research Institute of Chemical Technology, Daejun, Rep. of Korea

[21] Appl. No.: 445,186

[22] Filed: Dec. 1, 1989

[30] Foreign Application Priority Data

Dec. 3, 1988 [KR] Rep. of Korea ............... 16096/1988
Dec. 5, 1988 [KR] Rep. of Korea ............... 16160/1988

[51] Int. Cl.$^5$ .................... A61F 13/15; D03D 3/00; D04H 1/04
[52] U.S. Cl. .................... 604/364; 604/376; 536/3; 428/224; 428/296
[58] Field of Search .................... 536/3; 428/224, 296; 604/364, 374, 376

[56] References Cited

U.S. PATENT DOCUMENTS

| | | | |
|---|---|---|---|
| 2,688,586 | 3/1950 | Eberl et al. | 536/3 |
| 2,902,479 | 9/1959 | McNeely et al. | 536/3 |
| 3,521,638 | 7/1970 | Parrish | 604/364 |
| 3,756,232 | 9/1973 | Noguchi et al. | 604/364 |

Primary Examiner—Stephen C. Pellegrino
Assistant Examiner—Gary Jackson
Attorney, Agent, or Firm—Christie, Parker & Hale

[57] ABSTRACT

This invention is a catamenial pad or a tampon or a diaper which contains carboxymethylalginate (CMA) and alginic acid salt. The pad or diaper can be made from fibers composed of CMA alone or a mixture of CMA and alginic acid salt. CMA may be prepared by reacting chloroacetic acid, NaOH, and an alginic acid salt dispersed in a liquid aliphatic alcohol. More in detail, CMA can be prepared by a reaction in which sodium alginate is dispersed into ethanol, reacted with NaOH and chloroacetic acid at 40°–50°C. with agitation. The CMA can be spun into fibers and then it can be prepared into non-woven fabric. The fabric pad or diaper can be made into various designs. The fabric or the fiber has high absorbency, water-retentivity, stability, and coagulating ability against blood.

10 Claims, No Drawings

ALGINIC

BACKGROUND OF THE INVENTION

The present invention relates to a catamenial pad or tampon or a diaper containing carboxymethyl alginate (CMA) and alginic acid salt.

Particular characteristics of a pad or a diaper made of fabrics from carboxymethyl alginate and alginic acid salt fibers are high absorbency and water-retentivity.

Natural materials such as cotton, pulp, and sponges made of synthesized polymers have been used as the absorption materials for a long time. Absorbing mechanisms are known as water-absorbing through capillary action. The absorbency is about 20 times, but water-retentivity is reduced since the absorbed water may be removed easily under external stress.

In order to solve the aforementioned disadvantages and to provide a material having very high absorbency and water retentivity, there have been many proposed types of synthetic polymers. Generally, these polymers have a hundred times of its own weight in absorbency.

These polymers also have high water retentivity even under a tolerable degree of stress. These materials may be used in the field of sanitary products, agriculture, gardening and architecture, and many other attempts have been made to expand the usage ever since.

Water absorbable resin was first developed by the United States Department of Agriculture Research Laboratories in the 1960's. The resin was prepared by hydrolysis after copolymerization of starch with acrylonitrile. Using the above method, Henkel Corp. and Grain Processing Corp. (U.S. Corporations) began to produce the resin commercially in the late 1960's.

On the other hand, Sanyo Chemical Co., Ltd. (Japanese Corporation) succeeded in developing highly absorbent material by graft polymerization of acrylic acid with starch. Many other manufacturers have developed highly absorbent material from polyacrylic acid, polyvinyl alcohol (PVA), etc. In 1978, several manufacturers including Sanyo Chemical Co., Ltd. started pilot production of the material and in late 1978, sanitary products made of these highly absorbent materials appeared in the market. Thereafter, researches and experiments in this field were continuously carried out, leading to the development of the first paper pad made of this highly absorbent material. Later on, a paper diaper made of this material was developed.

Typically, these highly absorbent materials are supplied in two different forms. One is in the form of powder and the other is in the form of fiber. For example, the high absorbency resins in powder form may be taken from crosslinked compounds of polyacrylic acid salt, a graft copolymer of starch-acrylic salt (GSA) crosslinked compounds of PVA, and PVA/polyacrylic acid salt. The resins in fiber form may be taken from hydrolyzed polyacrylonitrile and crosslinked carboxymethyl cellulose (CMC). However, resins in the form of powder are difficult to process while resins in the form of fiber are easy to process and expensive but the absorbency is not as comparable.

In order to be used as sanitary products, a resin must have sufficient functions such as absorbency, water-retentivity, processability, and stability. The commercial sanitary products made of GSA or polyacrylamido sulfonic acid (PAAS) show relatively high absorbency in pure water. However, absorbency is reduced significantly to one tenth in salt solution.

Furthermore, processability of the resins in the form of powder are quite limited and can cause a pollution problem because of non bio-degradability. Although PVA/polyacrylic acid salt copolymer resin or starch-acrylic acid resin in the form of powder has sufficient gel-strength and thermal stability, these resins also have limited processability and have no bio-degradability.

Resins, like crosslinked CMC and hydrolyzed acrylonitrile can be spun into fiber and therefore processability is much better. However, absorbency is relatively low and the cost is 2-3 times more expensive than the resin in powder form.

SUMMARY OF THE INVENTION

There are two main objectives of the present invention. One is to provide a catamenial pad or tampon material which has excellent absorbency of menstrual blood.

The other objective is to provide a diaper material which has high absorbency of urine.

Other applications of the present invention will become obvious upon an understanding of the illustrative embodiments about to be described in the appended claims. Various advantages not referred to herein will occur to one skilled in the art upon employment of the invention in practice.

In order to achieve the aforementioned objectives, the present invention provides a pad or a diaper which contains CMA and alginic acid salt. The pad or the diaper can be made from fibers composed of CMA and alginic acid salt. The present inventors had proposed a method of preparing CMA in the U.S. patent application No. 07-379012 filed July 12, 1989. As mentioned in the specification of the application, CMA may be prepared by reacting chloroacetic acid, NaOH, and an alginic acid salt dispersed in a liquid aliphatic alcohol. More in detail, CMA can be prepared by a reaction in which sodium alginate is dispersed into ethanol, reacted with NaOH and chloroacetic acid at 40°-50° C. with agitation.

The CMA can be spun into fibers easily. Therefore, it has several advantages. From the fiber, non-woven fabric can be prepared which has good processability, and by using the non woven fabric, a pad or a diaper having various designs can be made easily.

Firstly, a pad may be formed into a panty which is lighter and more convenient than a sheet type.

Secondly, CMA is easily decomposed bio-chemically in the atmosphere, and therefore it may not cause pollution problems.

Thirdly, the fiber containing CMA has higher absorbability than the fiber form of crosslinked CMC and/or hydrolyzed acrylonitrile.

Lastly, the catamenial pad or tampon made of fabric containing CMA has excellent coagulating ability of menstrual blood. In order to prevent leakage of the blood because of the sudden increase of menstrual blood or of insufficient blood retentivity of the pad, various attempts have been made for modifying the design of the pad to increase the blood retentivity. However, the results of the attempts were not satisfactory. The aforementioned problem can be solved easily by applying CMA of the present invention, which has superior coagulating ability, to blood, or to the sanitary pad. CMA may coagulate the blood rapidly with calcium ions (blood coagulating factor) contained therein.

PREFERRED EMBODIMENTS OF THE INVENTION

Now, the present invention will be described more in detail referring to the preferred embodiments thereof.

EXAMPLE 1

Preparation of CMA 3,000 g of 40% ethanol and 1,500 g of toluene were added to 720 g of alginic acid in a rotary blender and the mixture was agitated vigorously to disperse the alginic acid. As a result, the alginic acid was dispersed well in the dispersing agent.

After stopping agitation, 510 g of 30% NaOH was added slowly with 5 minute intervals during a total of 30 minutes, and the mixture was agitated vigorously. Water that was produced during the reaction was absorbed by ethanol and thereby the reverse reaction was minimized. After stopping agitation, 470 g of chloroacetic acid was added to the mixture slowly and the temperature of the mixture was retained at 35° C. In order to adjust the pH of the solution, a predetermined amount of $Na_2CO_3$ was added to the mixture until the pH reached 8. After agitating the mixture for 50 minutes at 35° C., the mixture was cooled down below 10° C. and then the agitation was stopped. After removing the liquid, 1,500 g of 95% ethanol was added to the obtained residue, and then filtered again. The residues, CMA, were dried at 120° C. The yield was 76% or 1025 g. The degree of etherification of CMA in the present invention depends upon reaction conditions. The degree of etherification of CMA is preferably not less than 0.64. The calculation formula of the degree is as follows.

$$A = \frac{(25 \text{ ml} - X \text{ ml}) \times 0.4}{\text{weight of sample (g)}}$$

wherein,

A: milliequivalent of acid consumed per gram of sample

X: volume of hydrochloric acid consumed in ml

Degree of etherification $= 0.176 \times A \, (1 - 0.058 \times A)$

EXAMPLE 2

Preparation of fibers from CMA

The CMA prepared in Example 1 was dissolved in distilled water to make 2% solution and can be spun into fiber using a wet spinning machine. Preferable conditions of the spinning were as follows:

Spinning pressure: 0.5–1.0 Kgf/cm
Spinning speed: 5–8 m/min.
L/D of spinning nozzle: 110
Diameter of nozzle: 100 μm In the coagulating bath, coagulating solutions containing $CaCl_2$ were circulated continuously during the spinning process. Spun and coagulated fibers were drawn and dried by a drawing roller through which fibers were obtained. Non-woven fabric was prepared with the fibers using a needle punch machine.

EXAMPLE 3

Washing process of Non-woven CMA

A washing solution was prepared from the mixture of 100 g of isopropanol, 400 g of water, and 50 g of sodium acetate as a solvent for calcium. After spraying the washing solution on the non-woven fabrics prepared in Example 2, the fabric became wet and was left at 40° C. for 30 minutes. Then, the fabric was tilted at 45 degrees for 30 minutes to get rid of the washing solution. 50% ethanol with an amount of 100 times the weight of the fabric was poured on the fabric and thereby the unreacted washing solution was washed off from the fabric. The treatment was repeated 3 times. 80% ethanol was poured slowly on the non woven fabric, preventing the adhesion of the fibers. Then the fabric was tilted again at an angle of 45 degrees to get rid of the remaining washing solution. After that, the fabric was dried at 60° C. for 20 minutes.

A pad was made with the non-woven fabric prepared in the above Example 3. Also, a diaper was made with the same material. Absorbency tests of the pad and diaper were done by the Tea bag method, and the results are shown in Table 1.

TABLE 1

| CONTENTS | | Water absorbency (ml/g) | Menstrual blood absorbency (ml/g) | Urine absorbency (ml/g) |
| --- | --- | --- | --- | --- |
| Alginic acid salt (%) | Carboxymethylalginate (%) | | | |
| 100 | TD | 38 | 20 | 27 |
| 90 | 10 | 46 | 25 | 29 |
| 70 | 30 | 60 | 25 | 32 |
| 50 | 40 | 75 | 27 | 32 |
| 30 | 70 | 88 | 27 | 35 |
| 10 | 90 | 106 | 28 | 38 |
| — | 100 | 110 | 30 | 38 |

CMA, prepared in Example 1, was blended with alginic acid in the various ratios. The fibers and non-woven fabrics were prepared by repeating the methods of Examples 2 and 3. The pads and diapers were made with the fabrics. An absorbency test was performed by the Tea bag method and the results are also shown in the Table 1. Table 1 shows that the absorbency was increased with the increasing of the contents of CMA. It might be due to the result of ion concentration increase in the fabric which has a high carboxymethyl group content. However, the low absorbency in the solution having external electrolytes such as menstrual blood is the result of decreasing the osmotic pressure by the electrolytes in the salt solution. With the consideration of absorbency and production cost, 70–100% of CMA fiber may be practical for application.

COMPARISON TEST 1

Absorbency Test

A comparative test on the absorbency of a pad of the present invention with commercial products was done by the Tea bag method and the results are shown in Table 2. As shown in Table 2, the pad of the present invention shows higher absorbency than others.

TABLE 2

| | Water absorbency (ml/g) | Menstrual blood absorbency (ml/g) |
| --- | --- | --- |
| CMA pad of the present invention | 105 | 30 |
| Sample 1 ("Sopia", Product of Ssangyong corp., Korea) | 68 | 20 |
| Sample 2 ("Freedom", Product of Yuhan Kimbery, Korea) | 33 | 22 |
| Sample 3 ("Kotex", Product of | 47 | 26 |

TABLE 2-continued

| | Water absorbency (ml/g) | Menstrual blood absorbency (ml/g) |
|---|---|---|
| Yuhan Kimbery, Korea) | | |

COMPARISON TEST 2

Blood Coagulating Test

In order to compare the blood coagulation of a pad of the present invention with the pads in the market, blood coagulating tests were conducted by using the whole-blood coagulating method, and the results thereof are shown in Table 3.

TABLE 3

| | Time of whole-blood coagulation (min) |
|---|---|
| CMA pad of the present invention | 1.8 |
| Sample 1 ("Sopia") | 5.4 |
| Sample 2 ("Freedom") | 8.2 |
| Sample 3 ("Kotex") | 6.8 |

COMPARISON TEST 3

Urine Absorbability Test

In order to compare the urine absorbability of a diaper of the present invention with diapers in the market, urine absorbability tests were carried out in accordance with the Tea bag method, and the results thereof are shown in Table 4.

TABLE 4

| | Water absorbency (ml/g) | Urine absorbency (ml/g) |
|---|---|---|
| CMA of the present invention | 105 | 36 |
| Sample 1 ("Huggies", Product of Yuhan Yanghang, Korea) | 68 | 32 |
| Sample 2 ("Korebebe", Product of Yuhan Yanghang, Korea) | 47 | 30 |
| Sample 3 ("Jumbo", Product of Ssangyong corp., Korea) | 33 | 28 |

As shown in Table 4, the CMA of the present invention showed better urine absorbability than the other diaper materials.

What is claimed is:

1. An absorbent nonwoven fabric comprising carboxymethylalginate fibers prepared by spinning an aqueous solution of carboxymethylalginate, wherein the degree of etherification of carboxymethylalginate is not less than 0.64.

2. A catamenial pad comprising an absorbent nonwoven fabric comprising carboxymethylalginate fibers.

3. A pad as claimed in claim 2, wherein the content of carboxymethylalginate fibers is in the range of 1-100% by weight.

4. A pad as claimed in claim 3, wherein the content of carboxymethylalginate fibers is in the range of 70-100% by weight.

5. A diaper comprising an absorbent nonwoven fabric comprising carboxymethylalginate fibers.

6. A diaper as claimed in claim 5, wherein the degree of etherification of carboxymethylalginate is not less than 0.64.

7. A diaper as claimed in claim 5, wherein the content of carboxymethylalginate fibers is in the range of 1-100% by weight.

8. A diaper as claimed in claim 7, wherein the content of carboxymethylalginate fibers is in the range of 70-100% by weight.

9. A tampon comprising an absorbent nonwoven fabric comprising carboxymethylalginate fibers.

10. A tampon as recited in claim 9, wherein the degree of etherification of carboxymethylalginate is not less than 0.64.

* * * * *